United States Patent
Wulf

(10) Patent No.: US 10,105,104 B2
(45) Date of Patent: Oct. 23, 2018

(54) METHOD AND DEVICE FOR DETERMINING A DURATION OF A CRITICAL STATE OF A DRIVER OF A VEHICLE

(71) Applicant: Robert Bosch GmbH, Stuttgart (DE)

(72) Inventor: Felix Wulf, Ludwigsburg (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/647,740

(22) Filed: Jul. 12, 2017

(65) Prior Publication Data

US 2018/0028120 A1    Feb. 1, 2018

(30) Foreign Application Priority Data

Jul. 26, 2016    (DE) ........................ 10 2016 213 671

(51) Int. Cl.

| | |
|---|---|
| A61B 5/00 | (2006.01) |
| A61B 5/103 | (2006.01) |
| A61B 5/18 | (2006.01) |
| G06F 19/00 | (2018.01) |
| A61B 5/16 | (2006.01) |

(52) U.S. Cl.
CPC .......... *A61B 5/6893* (2013.01); *A61B 5/0077* (2013.01); *A61B 5/103* (2013.01); *A61B 5/163* (2017.08); *A61B 5/18* (2013.01); *A61B 5/7275* (2013.01); *A61B 5/746* (2013.01); *G06F 19/00* (2013.01); *A61B 5/168* (2013.01); *B60W 2540/22* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,900,819 A | * | 5/1999 | Kyrtsos | G08B 21/06 180/272 |
| 7,830,266 B2 | * | 11/2010 | Nakagoshi | G08B 21/06 340/575 |
| 9,905,108 B2 | * | 2/2018 | Kaplan | G08B 21/06 |
| 2009/0027212 A1 | * | 1/2009 | Nakagoshi | G08B 21/06 340/575 |

FOREIGN PATENT DOCUMENTS

| | | |
|---|---|---|
| DE | 19715519 A1 | 11/1997 |
| DE | 19803158 C1 | 5/1999 |
| DE | 102008056343 A1 | 5/2010 |
| DE | 102015117620 A1 | 4/2016 |

* cited by examiner

*Primary Examiner* — Travis R Hunnings
(74) *Attorney, Agent, or Firm* — Norton Rose Fulbright US LLP; Gerard Messina

(57) ABSTRACT

A method for determining a duration of a critical state of a driver of a vehicle. In this method, a state signal is read in, which represents a state of the driver detected using a sensor unit of the vehicle. It is subsequently checked whether the state signal represents the critical state or a non-critical state of the driver. If the state signal represents the critical state, a counter value of a counter representing the duration of the critical state is incremented. If the state signal represents the non-critical state, the counter value is held constant. If after the expiration of a reference hold time the state signal represents the non-critical state, the critical value is decremented.

20 Claims, 2 Drawing Sheets

METHOD AND DEVICE FOR DETERMINING A DURATION OF A CRITICAL STATE OF A DRIVER OF A VEHICLE

CROSS REFERENCE

The present application claims the benefit under 35 U.S.C. § 119 of German Patent Application No. DE 102016213671.2 filed on Jul. 26, 2016, which is expressly incorporated herein by reference in its entirety.

BACKGROUND INFORMATION

The present invention is directed to a device, method and computer program for determining a duration of a critical state of a driver of a vehicle A vehicle may be equipped with a warning system for warning a driver of fatigue or microsleep.

SUMMARY

A method for determining a duration of a critical state of a driver of a vehicle, a device which uses this method, and finally a corresponding computer program are provided.

Advantageous refinements of and improvements on the device, method and computer program are described herein.

An example method for determining a duration of a critical state of a driver of a vehicle is provided, the method including the following steps:

reading in a state signal, which represents the state of the driver detected using a sensor unit of the vehicle;

checking whether the state signal represents the critical state or a non-critical state of the driver;

incrementing a counter value of a counter representing the duration of the critical state when the state signal represents the critical state;

holding the counter value constant when the state signal represents the non-critical state; and decrementing the counter value when the state signal represents the non-critical state after expiration of a reference hold time.

A critical state may be understood to mean a state of a driver, as a result of which a fitness to drive of the driver is impaired. The critical state may, in particular, be a state, for example, in which the eyes of the driver are closed for a longer duration, for example, longer than the duration of a blink of the eye. Accordingly, a non-critical state may be understood to mean a state of the driver, in which the fitness to drive of the driver is unimpaired. The vehicle may be equipped with a sensor unit for monitoring the driver. The sensor unit, for example, a camera or an infrared sensor, may be designed to monitor a head area of the driver, in particular, an eye area of the driver. A state signal may be understood to mean a signal generated using a sensor unit. A counter may, for example, be understood to mean a digital counting mechanism or a software counter. A reference hold time may be understood to mean a predefined maximum duration, during which the counter value may be held constant. The reference hold time may lie, for example, between 0.1 sec and 0.5 sec.

The approach presented herein is based on the finding that a resetting of a counter for determining a cumulative duration of a critical state of a driver may be delayed. This has the advantage that short oscillations of an input signal representing the critical state may be bridged, without the counter being reset each time. Thus, a microsleep may be detected early in a driver, who only briefly opens the eyes and subsequently closes them again. In addition, inadequacies of the input signal may be bridged so that the microsleep may be detected even in the case of a momentarily failing signal. The approach presented herein therefore enables an efficient and robust detection of the duration of the critical state even in the case of momentary sensor errors.

According to one specific embodiment, it is checked in the step of checking whether the state signal represents a closed state of the eyes of the driver as the critical state or an opened state of the eyes as the non-critical state. In this way, it may be checked whether the driver is driving with open or closed eyes.

According to another specific embodiment, the counter value may be further incremented in the step of incrementing, if during checking it is revealed that the state signal subsequent to being held constant or, additionally or alternatively, subsequent to being decremented, again represents the critical state. In this way, the duration of the critical state may be cumulated.

It is further advantageous if in the step of incrementing, the counter value is incremented essentially linearly. In this way, the duration of the critical state may be ascertained with minimal computing effort.

The method may also include a step of ascertaining of a hold time, during which the counter value is held constant. In a step of comparing, the hold time and the reference hold time may be compared with one another, in order to ascertain a deviation between the hold time and the reference hold time. In the step of decrementing, the counter value may be decremented, if the comparison reveals that the hold time is longer than the reference hold time. Similarly, in the step of checking, the state signal may be checked again, if the comparison reveals that the hold time is shorter than the reference hold time. With this specific embodiment, it is possible to ascertain the duration of the critical state rapidly and with minimal memory requirements.

It is further advantageous if in a step of determining, a deviation between the counter value and a limiting value is determined. In this case, a warning signal for warning the driver may be output in a step of outputting as a function of the deviation between the counter value and the limiting value. A limiting value may, for example, be understood to mean a threshold value representing a microsleep. With this specific embodiment, it is possible to warn the driver early of the critical state.

According to another specific embodiment, the counter value may be set to zero in the step of decrementing. In this way, the counter may be easily reset.

This method may, for example, be implemented in software or hardware or in a mixed form of software and hardware, for example, in a control unit.

The approach presented herein also provides a device, which is designed to carry out, control or implement the steps of a variant of the method presented herein in corresponding units. With this embodiment variant of the present invention in the form of a device as well, it is possible to rapidly and efficiently achieve the object underlying the present invention.

For this purpose, the device may include at least one processing unit for processing signals or data, at least one memory unit for storing signals or data, at least one interface to a sensor or to an actuator for reading in sensor signals from the sensor or for outputting data signals or control signals to the actuator and/or at least one communication interface for reading in or outputting data, which are imbedded in a communication protocol. The processing unit may, for example, be a signal processor, a microcontroller or the like, whereby the memory unit may be a flash memory, an EPROM or a magnetic memory unit. The communication interface may be designed to read in or output data wirelessly and/or hard-wired, whereby a communication interface, which is able to read in or output hard-wired data, may read in these data, for example, electrically or optically from a corresponding data transmission line or output them in a corresponding data transmission line.

A device in the present case may be understood to mean an electrical device, which processes sensor signals and outputs control signals and/or data signals as a function thereof. The device may include an interface, which may be designed as hardware and/or software. In a hardware design, the interfaces may, for example, be part of a so-called system ASIC, which includes a wide variety of functions of the device. It is also possible, however, that the interfaces are dedicated, integrated circuits or are made up at least partially of discrete elements. In a software design, the interfaces may be software modules, which are present on a microcontroller, for example, in addition to other software modules.

In one advantageous embodiment, a control of the vehicle by the device takes place. For this purpose, the device may, for example, access sensor signals such as acceleration signals, pressure signals, steering angle signals or surroundings sensor signals. The control takes place via actuators, such as brake actuators, steering actuators or an engine control unit of the vehicle.

Also advantageous is a computer program product or computer program having program code, which may be stored on a machine-readable medium or memory medium, such as a semiconductor memory, a hard disk memory or an optical memory, and which is used for carrying out, implementing and/or controlling the steps of the method according to one of the previously described specific embodiments, in particular, when the program product or program is executed on a computer or a device.

Exemplary embodiments of the present invention are depicted in the figures and explained in greater detail below.

DETAILED DESCRIPTION OF EXAMPLE EMBODIMENTS

Figure 1:
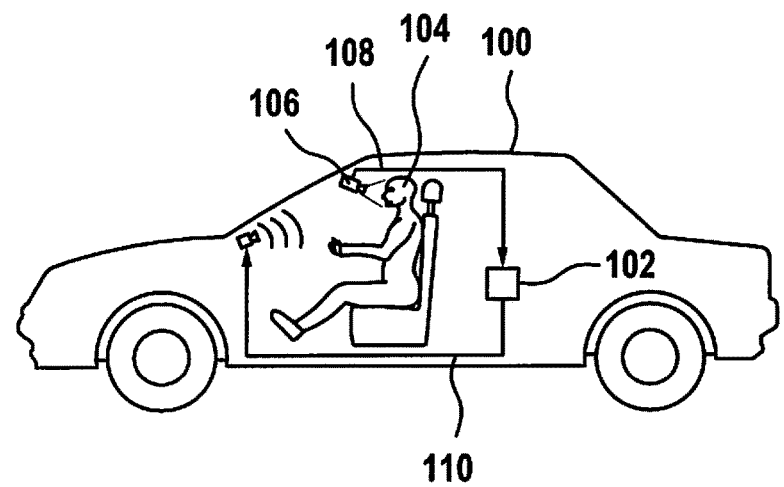
FIG. 1 schematically shows a depiction of a vehicle including a device according to one exemplary embodiment.

In the following description of preferred exemplary embodiments of the present invention, identical or similar reference numerals are used for elements which are represented in the various figures and act similarly, a repeated description of these elements being omitted.

FIG. 1 schematically shows a depiction of a vehicle 100 including a device 102 according to one exemplary embodiment. Device 102 is used to determine a duration of a critical state of a driver 104 of vehicle 100. For this purpose, device 102 is connected to a sensor unit 106, in this case a camera, for observing a face of driver 104. According to this exemplary embodiment, sensor unit 106 is designed to transmit a state signal 108 representing a state of driver 104 to device 102. The state is, for example, an open or closed state of the eyes of driver 104. Device 102 is designed to ascertain the duration of the critical state, for example, of the closed state of the eyes using state signal 108. In the process, device 102 cumulates the duration of the critical state with the aid of a counter when state signal 108 represents the critical state. If, on the other hand, state signal 108 represents a non-critical state of the driver, for example, the opened state of the eyes, device 102 then initially holds the duration of the critical state constant. Device 102 resets the counter only if the duration of the non-critical state exceeds a predefined reference hold time $t_h$.

According to the exemplary embodiment shown in FIG. 1, device 102 is designed to output a warning signal 110 depending on the duration of the critical state, in this case an acoustic warning signal, with which driver 104 may be warned of the critical state.

Figure 2:
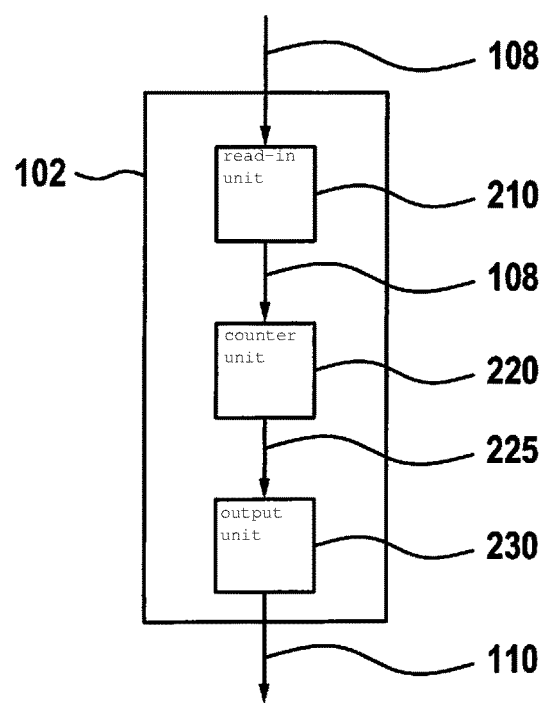
FIG. 2 schematically shows a depiction of a device according to one exemplary embodiment.

FIG. 2 schematically shows a depiction of a device 102 according to one exemplary embodiment, for example, of a device, as it is described above with reference to FIG. 1. Device 102 includes a read-in unit 210 for reading in state signal 108. Device 102 further includes a counter unit 220, in short, counter, which is designed to receive state signal 108 from read-in unit 210 and to output a counter value 225 representing the duration of the critical state using state signal 108. In this case, counter unit 220 is designed to initially check whether state signal 108 represents the critical state or the non-critical state of the driver. As long as state signal 108 represents the critical state, counter unit 220 increments counter value 225. Counter value 225 thus represents a cumulative duration of the critical state. As soon as the check of state signal 108 reveals that state signal 108 represents the non-critical state, the increase by counter unit 220 is stopped and counter value 225 is held constant. If the duration of the non-critical state exceeds the reference hold time $t_h$, then counter unit 220 sets counter value 225 to a lower value, for example, to zero.

If the check of state signal 108 reveals that state signal 108 again represents the critical state before expiration of the reference hold time $t_h$, the increase of constant held counter value 225 is then continued by counter unit 220, for example, until the check of state signal 108 reveals that state signal 108 again represents the non-critical state. Thus, counter value 225 may continue to be incremented with interruptions until reference hold time $t_h$ is exceeded during a phase of state signal 108 indicating the non-critical state.

According to one optional exemplary embodiment, device 102 includes an output unit 230, which is designed to receive counter value 225 from counter unit 220 and to compare this value with a limiting value, which represents, for example, a microsleep of the driver. If the comparison reveals that counter value 225 exceeds the limiting value, output unit 230 then outputs warning signal 110 for warning the driver.

Figure 3:
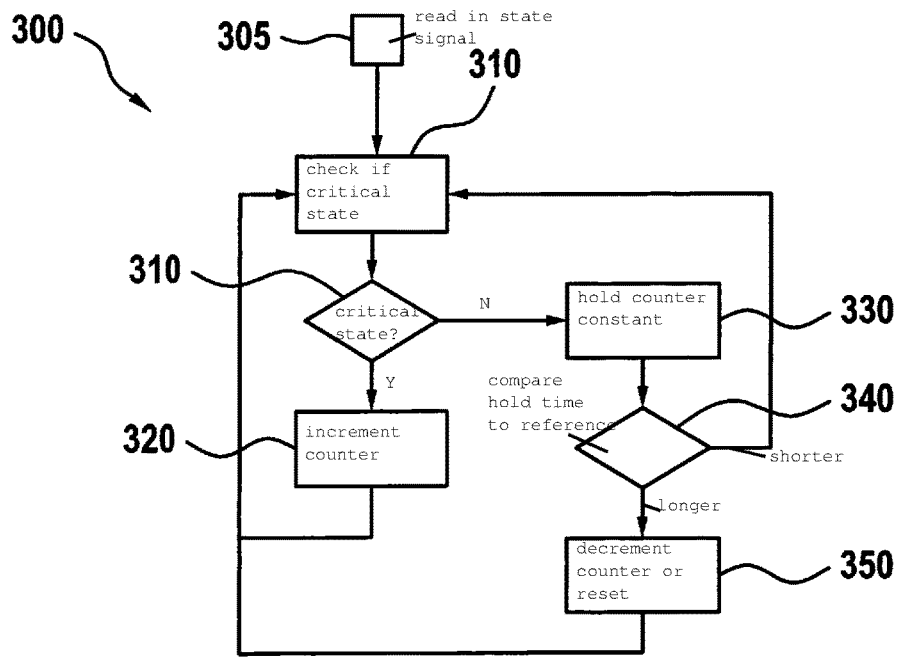
FIG. 3 schematically shows a depiction of a method according to one exemplary embodiment.

FIG. 3 shows a flow chart of a method 300 according to one exemplary embodiment. Method 300 may be carried out in conjunction with a device as it is described above with reference to FIGS. 1 and 2. An exemplary sequence of a calculation specification for determining the duration of the critical state is shown. In this sequence, the state signal is read in in a step 305. Subsequently, it is checked in a step 310 whether the state signal represents the critical state, also called event, or the non-critical state. In the case of an event, the counter value of the counter is incremented in a step 320, the state signal being re-checked in response to the increase in step 310. Otherwise, the counter value is held constant in a step 330. In this case, a hold time $t_e$, for example, elapsed since a last event, is ascertained, the counter value being held constant during hold time $t_e$. In a step 340, hold time $t_e$ is compared with reference hold time $t_e$ in order to ascertain a deviation between hold time $t_e$ and reference hold time $t_h$. If it is revealed in this case that hold time $t_e$ is longer than reference hold time $t_h$, the counter is then reset or decremented in a step 350. Step 310 is carried out again in response to the resetting or reduction. If, on the other hand, it is revealed that hold time $t_e$ is shorter than reference hold time $t_h$, step 310 is then directly repeated without resetting or decrementing the counter.

The individual steps of method 300 may be continuously carried out.

Figure 4:
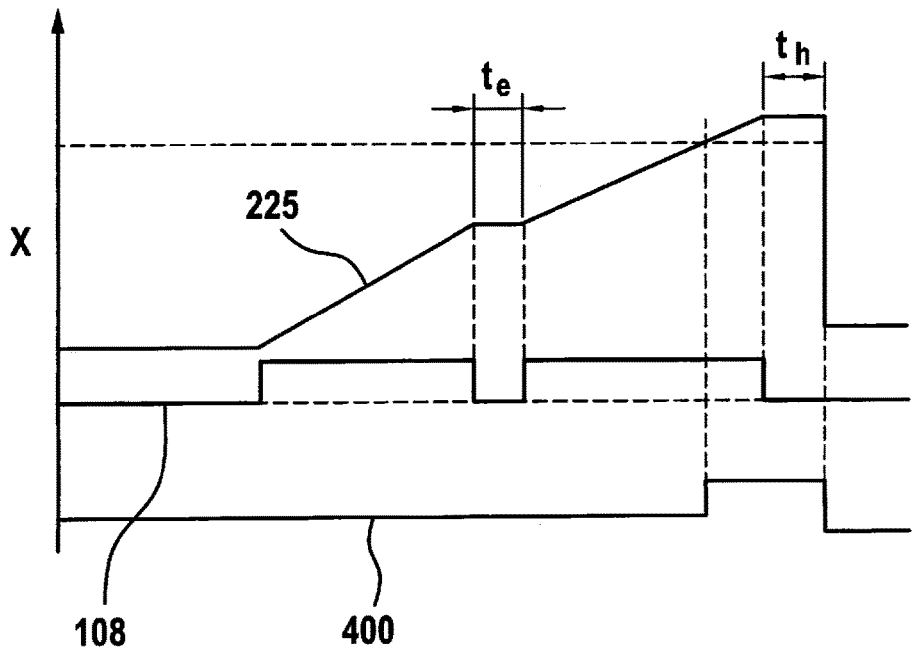
FIG. 4 shows a diagram for representing by way of example a cumulative duration of a critical state.

FIG. 4 shows a diagram for depicting by way of example, a cumulative duration of a critical state. The duration of the critical state may be cumulated, for example, using a device as it is described above with reference to FIGS. 1 and 3. A curve representing counter value 225 is shown. Plotted below the curve of counter value 225 is a profile of state signal 108, which here has, as an example, the profile of a square-wave signal. At the beginning of the calculation, counter value 225 equals zero. After a short time, state signal 108 increases abruptly to a value which represents the critical state, i.e., here, the closed state of the eyes. In this case, counter value 225 begins to increase essentially linearly. Subsequently, state signal 108 drops abruptly to zero and remains at zero for a duration, which is shorter than reference hold time $t_h$. During this duration, also referred to above as hold time $t_e$, counter value 225 remains constant. Subsequently, state signal 108 again abruptly increases to the value representing the critical state, so that counter value 225 again increases essentially linearly, starting from a last ascertained value. In the process, counter value 225 exceeds a threshold value x, also referred to above as limiting value, which results in the generation of a microsleep signal 400. A profile of microsleep signal 400, here also a square-wave signal, is plotted below the profile of state signal 108. Counter value 225 then increases further towards the exceedance of threshold value x, until state signal 108 finally again drops to zero, so that counter value 225 incremented in the meantime remains constant. Hold time $t_e$ in this case exceeds reference hold time $t_h$, which results in the resetting of the counter. Accordingly, counter value 225 drops abruptly to zero. Thus, microsleep signal 400 is also no longer present.

The approach presented herein is summarized once again below in other words with reference to FIGS. 1 through 4.

First, the detection of the critical state "eyes closed" takes place in step 310. This is followed by the calculation of the duration of the critical state. In this process, the time duration for which the state "eyes closed" is present is calculated. This takes place with the aid of a counter, which cumulates the time as long as the eyes are classified as closed in the previous step.

Once the eyes are classified as open again in step 310, the counter is set to zero and begins again with the next closing of the eyes. The value of the counter then represents the cumulative duration of the state "closed eyes."

In this case, a hysteresis is then built in, which is able to bridge short oscillations of state signal 108, without the counter being reset each time to zero. This has the advantage that a microsleep may be detected earlier in the case of a driver, who only briefly opens his/her eyes and subsequently closes them again. In addition, inadequacies of the input signals may be bridged in this way, so that microsleep may be detected, even in the case of momentarily failing input signals.

To efficiently calculate the duration of the critical state, the calculation specification shown, for example, in FIG. 3, is used. In this case, the counter is incremented in accordance with the time duration since a last check, depending on the presence of the critical state, also referred to as an event. If this calculation specification is carried out in a constant and determinate cycle time, the duration between the cycles is used here for incrementing the counter. This method has the advantage that only one memory element, namely, the counter, is required for calculating the duration of the critical state. In this way, the duration may be very efficiently calculated.

It may happen that the critical state is not detected for short periods of time. Instead, the non-critical state in which the eyes are open may be erroneously detected or no detection is possible at all. In these cases, the counter would be erroneously set to zero again, which makes a detection of longer critical states, for example, of a microsleep, impossible. To solve this problem, reference hold time $t_h$ is then introduced in order to make the calculation robust with respect to momentary sensor errors. In the absence of the critical state, the state of the counter is maintained for a certain period of time in such case. Only after expiration of reference hold time $t_h$ is the counter reset or decremented. The result of such a calculation is depicted in FIG. 4. The value range of reference hold time $t_h$ is selected as a function of the existing power of sensor unit 106 and of the detecting duration of the critical states. For example, $t_h$=0.2 sec may be set.

The output of a warning decision takes place generally based on the principle that a warning is given once threshold value x in the cumulative duration of the critical state is exceeded. A warning takes place, for example, if the duration of the critical state reaches 1 sec. Threshold value x is variable, for example, and is selected as a function of external parameters.

If an exemplary embodiment includes an "and/or" linkage between a first feature and a second feature, this is to be read in the sense that the exemplary embodiment according to one specific embodiment includes both the first feature and the second feature, and according to another specific embodiment, either only the first feature or only the second feature.

What is claimed is:

1. A method for determining a duration of a critical state of a driver of a vehicle, the method comprising:
   reading in a state signal, which represents a state of the driver detected using a sensor unit of the vehicle;
   checking whether the state signal represents the critical state or a non-critical state of the driver;
   incrementing a counter value of a counter representing the duration of the critical state when the state signal represents the critical state;
   holding the counter value constant when the state signal represents the non-critical state;
   decrementing the counter value when the state signal represents the non-critical state after expiration of a reference hold time; and
   performing at least one of:
   (i) ascertaining a hold time during which the counter value is held constant, the hold time and the reference hold time being compared with one another in a task of comparing to ascertain a deviation between the hold time and the reference hold time, the counter value being decremented in the decrementing if the comparison reveals that the hold time is longer than the reference hold time, the state signal being checked again in the checking if the comparison reveals that the hold time is shorter than the reference hold time; and/or (ii) determining a deviation between the counter value and a limiting value, a warning signal for warning the driver being output in a task of outputting as a function of the deviation between the counter value and the limiting value.

2. The method of claim 1, wherein the checking includes checking whether the state signal represents a closed state of the eyes of the driver as the critical state or represents an open state of the eyes as the non-critical state.

3. The method of claim 1, wherein in incrementing, the counter value is further incremented if during checking it is revealed that the state signal again represents the critical state at least one of (i) subsequent to being held constant, and (ii) subsequent to being decremented.

4. The method of claim 1, wherein in the incrementing, the counter value is incremented linearly.

5. The method of claim 1, wherein (i) is performed.

6. The method of claim 1, wherein (ii) is performed.

7. The method of claim 1, wherein in the decrementing, the counter value is set to zero.

8. The method of claim 1, wherein (i) and (ii) are performed.

9. A device for determining a duration of a critical state of a driver of a vehicle, comprising:
   a processor configured to perform the following:
      reading in a state signal, which represents a state of the driver detected using a sensor unit of the vehicle;
      checking whether the state signal represents the critical state or a non-critical state of the driver;
      incrementing a counter value of a counter representing the duration of the critical state when the state signal represents the critical state;
      holding the counter value constant when the state signal represents the non-critical state;
      decrementing the counter value when the state signal represents the non-critical state after expiration of a reference hold time; and
      performing at least one of:
         (i) ascertaining a hold time during which the counter value is held constant, the hold time and the reference hold time being compared with one another in a task of comparing to ascertain a deviation between the hold time and the reference hold time, the counter value being decremented in the decrementing if the comparison reveals that the hold time is longer than the reference hold time, the state signal being checked again in the checking if the comparison reveals that the hold time is shorter than the reference hold time; and/or
         (ii) determining a deviation between the counter value and a limiting value, a warning signal for warning the driver being output in a task of outputting as a function of the deviation between the counter value and the limiting value.

10. The device of claim 9, wherein (i) is performed.

11. The device of claim 9, wherein (ii) is performed.

12. The non-device of claim 9, wherein (i) and (ii) are performed.

13. A non-transitory machine-readable memory medium having a computer program, which is executable by a processor, comprising:
   a program code arrangement having program code for determining a duration of a critical state of a driver of a vehicle, by performing the following:
      reading in a state signal, which represents a state of the driver detected using a sensor unit of the vehicle;
      checking whether the state signal represents the critical state or a non-critical state of the driver;
      incrementing a counter value of a counter representing the duration of the critical state when the state signal represents the critical state;
      holding the counter value constant when the state signal represents the non-critical state;
      decrementing the counter value when the state signal represents the non-critical state after expiration of a reference hold time; and
      performing at least one of:
         (i) ascertaining a hold time during which the counter value is held constant, the hold time and the reference hold time being compared with one another in a task of comparing to ascertain a deviation between the hold time and the reference hold time, the counter value being decremented in the decrementing if the comparison reveals that the hold time is longer than the reference hold time, the state signal being checked again in the checking if the comparison reveals that the hold time is shorter than the reference hold time; and/or
         (ii) determining a deviation between the counter value and a limiting value, a warning signal for warning the driver being output in a task of outputting as a function of the deviation between the counter value and the limiting value.

14. The non-transitory machine-readable memory medium of claim 13, wherein (i) is performed.

15. The non-transitory machine-readable memory medium of claim 13, wherein (ii) is performed.

16. The non-transitory machine-readable memory medium of claim 13, wherein (i) and (ii) are performed.

17. The non-transitory machine-readable memory medium of claim 13, wherein the checking includes checking whether the state signal represents a closed state of the eyes of the driver as the critical state or represents an open state of the eyes as the non-critical state.

18. The non-transitory machine-readable memory medium of claim 13, wherein in incrementing, the counter value is further incremented if during checking it is revealed that the state signal again represents the critical state at least one of (i) subsequent to being held constant, and (ii) subsequent to being decremented.

19. The non-transitory machine-readable memory medium of claim 13, wherein in the incrementing, the counter value is incremented linearly.

20. The non-transitory machine-readable memory medium of claim 13, wherein in the decrementing, the counter value is set to zero.

* * * * *